United States Patent [19]

Orchard et al.

[11] Patent Number: 4,572,672
[45] Date of Patent: Feb. 25, 1986

[54] SURFACE COATING CHARACTERIZATION METHOD AND APPARATUS

[75] Inventors: Stanley E. Orchard, Stoke Poges; Celia C. Taylor, Slough, both of England

[73] Assignee: Imperial Chemical Industries PLC, London, England

[21] Appl. No.: 462,454

[22] Filed: Jan. 31, 1983

[30] Foreign Application Priority Data

Feb. 19, 1982 [GB] United Kingdom ............... 8204933

[51] Int. Cl.⁴ .................... G01N 21/47; G01N 21/01
[52] U.S. Cl. .................................. 356/446; 356/244
[58] Field of Search ............. 356/445, 319, 405, 406, 356/446, 244; 364/526

[56] References Cited

U.S. PATENT DOCUMENTS

| | | |
|---|---|---|
| 3,690,771 | 4/1972 | Armstrong . |
| 3,708,233 | 1/1973 | Van Dyk et al. .................. 356/244 |
| 3,712,745 | 1/1973 | Armstrong, Jr. et al. .......... 356/244 |
| 4,097,160 | 6/1978 | Yataki et al. ........................ 356/446 |

FOREIGN PATENT DOCUMENTS

| | | |
|---|---|---|
| 1107822 | 3/1968 | United Kingdom . |
| 1401957 | 8/1975 | United Kingdom . |
| 1474191 | 5/1977 | United Kingdom . |
| 1254539 | 11/1977 | United Kingdom . |

OTHER PUBLICATIONS

N. J. Harrick, Internal Reflection Spectroscopy, 1967, John Wiley & Sons, Inc., pp. 76–81.
Van Oene et al. "Control of Alumium Flake in Metallic Color Paints"—Proc. 7th Int. Coating Conference, Athens 1981.
Hemmendinger et al., "A Goniospectrophotometer for Color Measurements", Proc. 1st. AIC Congress, Stockholm 1969.
Roberts et al., J. Coating Technology vol. 51, pp. 59–63 (Jun. 1979).

*Primary Examiner*—Vincent P. McGraw
*Assistant Examiner*—Robert D. V. Thompson, III
*Attorney, Agent, or Firm*—Cushman, Darby & Cushman

[57] ABSTRACT

Surface coating films containing metallic flake pigment are characterized by (a) illuminating the film with a parallel beam of light which is inclined at a given angle to the film normal and (b) measuring the intensity of light reflected from a point on the film at a plurality of azimuthal viewing positions located in a circle which lies in a plane parallel to the film and through the center of which passes the film normal at the point. Apparatus suitable for carrying out the measurements is described. The invention enables the frequency distribution of the orientations of the metallic flake in the film to be determined.

6 Claims, 3 Drawing Figures

SURFACE COATING CHARACTERIZATION METHOD AND APPARATUS

This invention relates to a method for characterising instrumentally a surface coating containing a metallic flake pigment, and to apparatus whereby the method may be carried out.

Surface coatings containing a metallic flake pigment, for example aluminium flake, are well known. They are especially favoured for the protection and decoration of automobile bodies, by reason of their imparting a differential light reflection effect, usually referred, to as "flip", dependent upon the angle from which the car body is viewed. The degree of flip effect achieved is a function of the orientation of the metallic flakes with respect to the outer surface of the coating film; ideally, the flakes should all lie in planes parallel to this surface, the maximum flip effect then being observed, but in practice it is not possible to obtain more than a proportion of the flakes lying truly parallel and the remainder lie at various, mostly small, angles to the surface plane, i.e. there is a distribution of the orientations of the flakes in the coating. Metallic coatings often contain in addition pigments other than metallic flake; such material is usually of a light-absorbing rather than a light-scattering type.

Instrumental characterisation of metallic pigmented coatings can in principle be carried out by measuring with a reflectometer the dependence on angle of the reflectance of a coated panel. In the past, this has been done by making measurements at a number of angles of incident illumination and of viewing angle, either in a single, fixed plane or with a fixed angle between them. The results of such measurements are indeed dependent on the degree of flake alignment but their value for characterising the coating is diminished by the fact that they are also dependent on the relative concentrations of the metallic flake and of any light-absorbing pigment present. For an effective measure of the degree of alignment of the metallic flakes to be obtained, therefore, it is necessary under these circumstances to allow for the absorption of any pigment present. Measurements can be made of the variation in reflectance that occurs when the coated panel is rotated about the panel normal, but these merely reveal any lack of symmetry in flake orientation about the film normal which may be the result of poor application and/or drying techniques. Thus this technique does not measure the actual distribution of flake orientation at any particular point.

We have now found that a useful measure of the distribution of metallic flake, which is not subject to these disadvantages or limitations, can be obtained by illuminating a plane specimen of the film at a fixed, predetermined angle to the film normal and measuring the intensity of the light reflected from the film surface also at a fixed angle to the film normal but at a plurality of different azimuthal viewing positions.

Thus according to the present invention there is provided a method for the characterisation of a surface coating film containing a metallic flake pigment, the method comprising the steps of (a) illuminating a plane specimen of the film with a parallel beam of light which is inclined at a given angle to the normal with respect to the film surface and (b) measuring the intensity of light reflected from the film at a plurality of azimuthal viewing positions.

By an "azimuthal viewing position" we mean a position for intercepting a beam of light reflected from a point on the film surface within the illuminated area thereof, the position being located in a circle which lies in a plane parallel to the film surface and through the centre of which circle the film normal at that point passes. Reference may be made here to the accompanying diagram FIG. 1, in which the incident light beam is represented by the line X and makes an angle $\theta_o$ with the normal Z to the film surface; the reflected beams are represented by the lines $Y_1$, $Y_2$, etc., each of which makes a common angle $\theta$ with the film normal Z.

Figure 1:
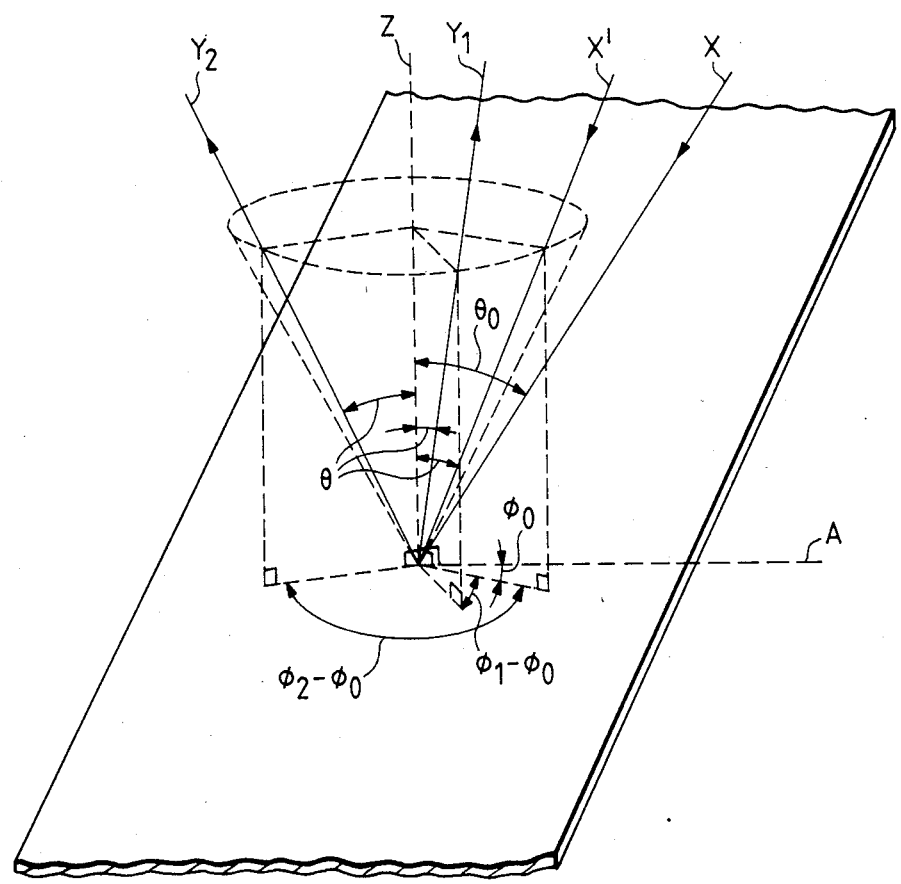
FIG. 1 shows incident and reflected beams of light with respect to the film normal.

The beam of light with which the film is illuminated may be produced by any conventional source in conjunction with suitable optical elements so that the beam satisfies the three requirements of (i) being parallel, (ii) being inclined at a given angle ($\theta_o$ as shown in FIG. 1) to the film normal and (iii) providing an area of illumination on the film surface which is larger than the area from which light is collected, at all azimuthal viewing positions. Preferably it is arranged that the illuminated area of the film surface is circular.

The measurement of the light that is reflected from the film may be carried out in a number of different ways. For example, it may be achieved by the use of a photodetector that is mounted in a manner permitting it to be moved in a circular path about the normal to the film at a point within the illuminated area thereof, the light-sensitive surface of the detector being directed so that it effectively views an area lying wholly within the said illuminated area and being maintained at a predetermined constant perpendicular distance l from the plane of the film and at a predetermined constant distance d from the axis of rotation (the said film normal), so that $d/l = \tan\theta$, where $\theta$ is the viewing angle relative to the film normal, and the film itself being held stationary. As the detector rotates, the intensity of the reflected light is measured at various values of the azimuthal angle or angle of rotation $\phi$ ranging from $\phi_o$, the angle of the incident beam as measured from some arbitrary base-line (denoted by A in FIG. 1), to $\phi_o + 180°$, i.e. diametrically opposite the incident beam. The number of values of $\phi$ at which the reflected light intensity is measured may vary considerably according to the particular film which is being characterised, depending mainly on the narrowness or breadth of the distribution of flake orientations in the film. At least four non-zero measurements will ordinarily be needed, of which one may be selected as a reference to which the others are expressed as proportional reflectance intensities.

Instead of moving the photodetector, the measurement of the reflected light may be made with the aid of a plane mirror which is mounted so as to be movable in the same manner as the photodetector in the previous description, the operational part of the reflecting surface of the mirror maintaining pre-determined, constant distances l and d as before. The photodetector is then kept stationary and the mirror is aligned so that the photodetector effectively views an area lying wholly within the illuminated area of the film. A constant proportion of the light arriving at the mirror from the film is then incident upon the detector, whatever the value of the angle $\phi$ may be within the range of measurement. This method of measurement is preferred rather than the one first described, since it avoids any problems of providing electrical contact with the photodetector during its motion. It is also preferred for the reason that it facilitates the use of a "double beam" procedure, whereby the intensity of the incident light can constantly be monitored by reference to a reflectance standard.

As an alternative to either of the foregoing procedures involving a single photodetector and a movable viewing element, measurement of the reflected light may be effected by means of a plurality of fixed viewing elements, located at suitably spaced intervals around the same circular path that is traversed by the single photodetector or the mirror in the previous cases. Each of the fixed viewing elements may itself be a photodetector, which directly receives the reflected light, or it may be an optical light-gathering system, such as an optical fibre, conveying the received light to one or more photodetectors located at some point remote from the actual viewing positions. This use of a plurality of viewing elements has the advantages of requiring no moving mechanism and of being faster in operation, but it clearly calls for rather more complicated circuitry for recording the light intensities detected than is required in the case of a single movable viewing element.

The series of reflected light intensities thus measured at the chosen number of different azimuthal viewing positions constitutes a simple form of characterisation of the film under examination. The success or failure of a test film to match the characteristics of a given standard can readily be established in an empirical fashion by making measurements upon each of them using the same incident light angle and the same set of azimuthal viewing positions in each case. The data obtained by means of steps (a) and (b) of the invention may, however, be utilised to derive the frequency distribution of the metallic flake orientations in a film by adopting the further steps of (c) expressing the intensity of light reflected at each azimuthal position as a proportion of the intensity of light reflected at some selected azimuthal position and (d) establishing the relationship between the proportional intensities so derived and the angles which the metallic flakes make with the film normal.

This extended method of the invention is based on the following theoretical considerations. From the laws of reflection it follows that, for a particular metal flake contained within the coating film, the direction of the flake normal will lie in a plane containing both the incident and the reflected light beams and will be equidistant from them both. Light is reflected from the illuminated flakes in many directions; the fraction of this reflected light that is contained in a small solid angle $d\omega$ around the direction $(\theta,\phi)$ can be written as $p(\theta,\phi; \theta_o, \phi_o) d\omega$ where $(\theta_o,\phi_o)$ is the incident direction. If $\alpha$ is the angle made by a particular flake normal with the film normal, the fraction of flake normals that is contained in a small solid angle $d\omega'$ around this angle $\alpha$ with the film normal can be written as $n(\alpha)d\omega'$.

Then $$n(\alpha) \, d\omega' \; \alpha \; p(\theta,\phi; \theta_o, \phi_o) \, d\omega,$$

the value of $\alpha$ being related to the values of $\theta$, $\phi$, $\theta_o$ and $\phi_o$ by the laws of reflection. Thus, from a knowledge of the fraction p over a suitable range of values of $\theta,\phi$, a measure of the distribution of flake orientation can be derived. What is in fact measured is the intensity of the light reflected from the film in the direction $(\theta,\phi)$. Given a constant intensity of the incident light an a fixed angle of incidence, the intensity of the reflected light will be proportional to the reflectance of the film as measured using this particular geometry.

In general, assuming the absence from the film of any significant quantities of light-scattering media other than the metallic flakes, it can be shown that, in the absence of surface reflection, the reflectance R relative to a perfectly white Lambertian diffuser is given to a first order of approximation by:

$$R = \psi \, (\theta, \theta_o) \, p \, (\theta,\phi; \theta_o, \phi_o),$$

where $\psi$ is a function of $\theta$ and $\theta_o$ but not of $\phi$ or $\phi_o$. Where there is surface reflection, an appropriate correction should be made. It is not necessary for the present purpose to define the nature of the function $\psi$. In general, $\psi$ is also a function of (a) the volume concentration of the metallic flakes in the film; (b) the distribution of the angles of orientation of the flakes; (c) the brightness of the flakes; (d) the concentrations and absorption coefficients of any other pigments in the film; and (e) the refractive index of the resin. If the reflectance is measured employing a fixed angle of incidence $\theta_o$ relative to the film normal and a constant viewing angle of $\theta$ to the film normal but at a range of different values of $\phi - \phi_o$ around the normal, and if the reflectances measured at these various values of $(\phi - \phi_o)$ are each divided by the reflectance measured at one selected value of 1 $(\phi - \phi_o)$, which for convenience may be designated $(\phi_s - \phi_o)$, a series of relative reflectances is derived, which is independent of $(\theta,\theta_o)$. That is, at constant values of $\theta$ and $\theta_o$, $$\frac{\text{Reflectance at } \phi - \phi_o}{\text{Reflectance at } \phi_s - \phi_o} = \frac{p(\theta, \phi; \theta_o, \phi_o)}{p(\theta, \phi_s; \theta_o, \phi_o)} = \frac{n(\alpha) \, d\omega'}{n(\alpha_s) \, d\omega'} = \frac{n(\alpha)}{n(\alpha_s)}$$

where $\alpha_s$ is the value of $\alpha$ which corresponds to the selected viewing angle $\phi_s$.

Accordingly, by measurement of the reflectance of the film at a plurality of azimuthal positions as described and calculation of the relative reflectances, a corresponding number of values for $n(\alpha)/n(\alpha_s)$ are obtained. The value of $\alpha$ for each of these can be calculated, from considerations of straightforward geometry, knowing the values of $\theta$, $\theta_o$, $\phi$ and $\phi_o$. The mathematical equation connecting $\alpha$ with these variables differs according to whether or not an experimental procedure is used, in measuring the reflectances, which avoids refraction at the film surface. A practical procedure which may be used for avoiding refraction employs a glass hemisphere of suitable dimensions and of a refractive index equal or close to that of the film binder, the hemisphere being placed upon the film surface within the illuminated area and with an intervening layer of a transparent oil having a similar refractive index. The procedure is further discussed below in connection with the apparatus according to the invention.

Where this procedure is adopted, the equation connecting $\alpha$ with $\theta$, $\theta_o$, $\phi$ and $\phi_o$ is as follows:

$$\cos^2\alpha = \frac{(\cos\theta + \cos\theta_o)^2}{2[1 + \cos\theta\cos\theta_o + \sin\theta\sin\theta_o\cos(\phi - \phi_o)]}$$

According to a preferred manner of operating the method of the invention, it is arranged that the angle made with the film normal by the incident light beam is equal to the viewing angle at which all the reflectance measurements are made, that is to say, $\theta_o$ is made equal to $\theta$ (the incident beam is then represented by the line X' in FIG. 1). The advantage of so doing is that it is then possible to obtain reflectance measurements relating to flakes oriented parallel to the film surface, i.e. for the case $\alpha = 0$. In this case, it is arranged that one of the reflectance measurements is actually made at the viewing position given by $\phi = \phi_o + 180°$, at which the observed reflectance will usually be a maximum; this position is then adopted as the reference position ($\phi_s - \phi_o$), so that all the measured reflectance intensities are expressed as a fraction of this maximum value.

Under these preferred conditions of measurement, the equation from which $\alpha$ may be calculated becomes:

$$\cos^2\alpha = \frac{2\cos^2\theta}{1 + \cos^2\theta + \sin^2\theta\cos(\phi - \phi_o)}$$

For the case where refraction at the film surface is not avoided, the appropriate equation is:

$$\cos^2\alpha = \frac{2\left(1 - \frac{1}{\mu^2}\sin^2\theta\right)}{2 - \frac{1}{\mu^2}\sin^2\theta[1 - \cos(\phi - \phi_o)]}$$

where $\mu$ is the refractive index of the binder. At the viewing position $\phi_s = \phi_o + 180°$, the value of $\alpha_s$ will be zero.

Corrections may be desirable to the measured reflectances to allow for known sources of error in the apparatus used, e.g. non-linearity of the photodetector.

Figure 2:
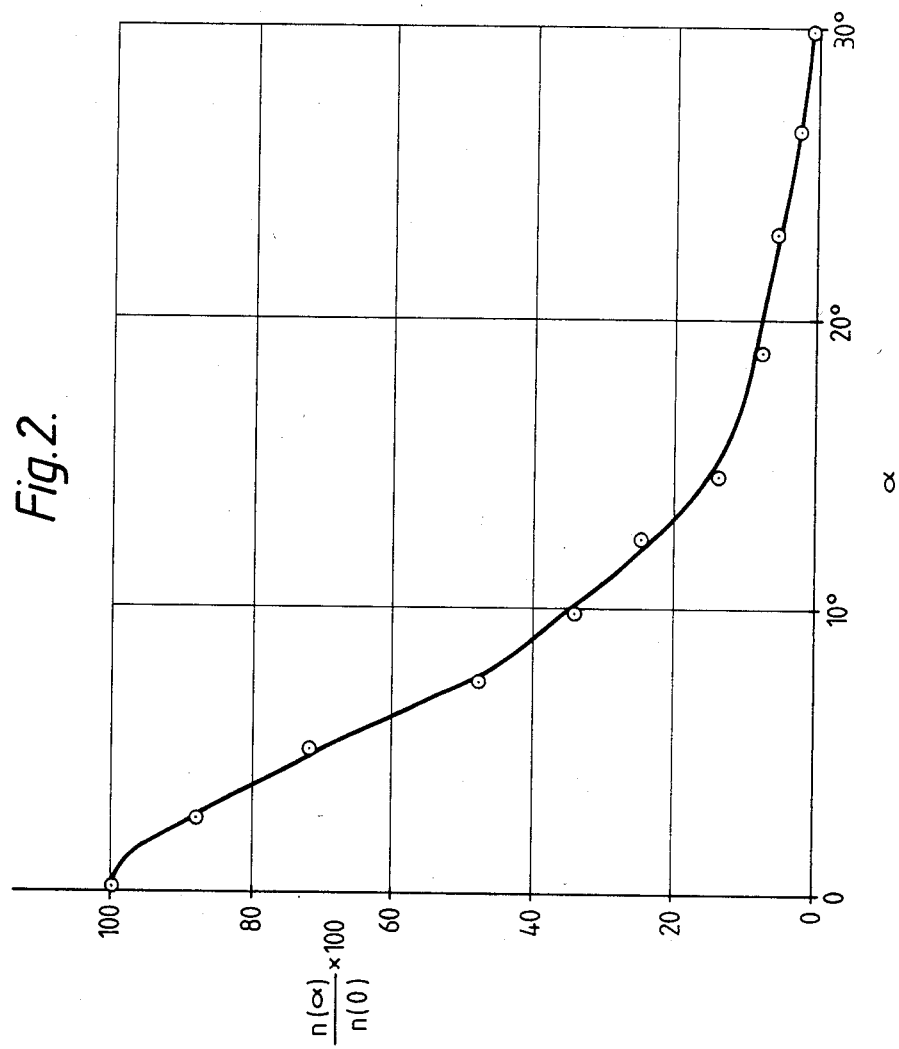
FIG. 2 shows a plot of the ratio of relative reflectances versus angle made by flake normal to the film normal.

Having calculated the appropriate series of values of $\alpha$, these may then be plotted graphically against the corresponding values of $n(\alpha)/n(O)$, giving a distribution curve for the metallic flake orientation. An example of such a curve and the data from which it is derived are shown in FIG. 2 and the accompanying table. Where the curve is complete and consequently can be normalised, it represents the absolute distribution of flake orientations, independently of any assumptions concerning the actual nature of the distribution $n(\alpha)$. Where the curve is incomplete, it represents rather the distribution relative to the number of flakes which are orientated parallel to the film surface. Knowledge of either the absolute or the relative distribution can be of considerable assistance in the formulation of metallic pigment coating compositions. Thus, for a given type of composition, the detailed formulation or conditions of application which are necessary in order to obtain the optimum 'flip' effect can be found by appropriate trials in conjunction with reflectance measurements made according to the method of the invention. In general, the steeper the fall of the distribution curve from the point defined by $n(\alpha)/n(O) = 100\%$, $\alpha = 0°$, the more pronounced the flip effect will be. Similarly, determination of the distribution by this method enables the accuracy of matching of an experimental composition to a given standard film to be determined.

It should be noted that, for a fixed value of $\theta$, the removal of the effect of refraction at the film/air interface allows the distribution to be characterised over a larger range of values of $\alpha$ than is the case when the effect is not removed. Whether or not the loss of part of the curve is significant in the overall assessment of the distribution will depend upon the particular circumstances, but in general it is preferred to remove the refraction effect and so obtain as complete a picture of the flake alignment as possible. It may be mentioned that one advantage of the method of the invention, as compared with the prior art techniques, is that a single allowance for refraction is valid for the incident beam and all the reflected beams irrespective of their azimuthal positions. In the prior art techniques, the allowance for refraction changes as the angles of the beams to the film normal vary.

According to a further aspect of the present invention, there is provided an apparatus suitable for the characterisation of a surface coating film containing a metallic flake pigment, the apparatus comprising a source for producing a parallel beam of light, a support for the film to be characterised so positioned that the beam is directed towards the film at a given angle to the normal with respect to the film surface and the film is illuminated thereby, and means for receiving and measuring the light reflected from an area of the film surface lying wholly within the illuminated area at a plurality of different azimuthal viewing positions as hereinbefore defined.

As already indicated above in discussing the method of the invention, in one embodiment of the apparatus a single means for receiving and measuring the reflected light is employed and this is movable in a circular path lying in a plane parallel to the film surface, so that it always views the illuminated area of the film surface at the same angle. The means in question may consist of a suitably mounted photodetector, the signals generated by which are amplified and passed to a recording instrument or meter, whereby a relative measure of the intensity of the reflected light is given. It may, however, be more convenient if the movable receiving and measuring means consists instead of a mirror which can traverse the prescribed circular path, together with a photodetector which is mounted in a fixed position such that the light reflected from a point on the film surface and subsequently by the mirror always falls upon it whatever the position of the mirror. Conveniently the motion of either the movable detector or the mirror in the circular path may be arranged to take place in discrete steps rather than progressively, the steps corresponding to the chosen number of different azimuthal viewing positions at which reflectance measurements are to be made. It is sufficient for the performance of the method of the invention if the motion of the detector or mirror covers a range of azimuthal angles extending as nearly as possible from $\phi = \phi_o$ to $\phi = \phi_o + 180°$, but it is advantageous if the detector or mirror is in fact capable of traversing almost the full 360° range. Ideally, the reflected intensities observed at the chosen azimuthal positions in the range 0°–180° will be repeated at the corresponding positions in the range 180°–360°, but in practice it is useful to take measurements throughout the full range in order to confirm the accurate and symmetrical functioning of the apparatus, and of the quality of the panel preparation. In the event that there is a small discrepancy between the corresponding measured values, the mean of each corresponding pair may be taken.

In an alternative embodiment of the apparatus of the invention, again as already indicated above, a plurality of means for receiving and measuring the reflected light are employed and these are located in fixed positions in a circular path lying in a plane parallel to the film surface, the number and position of the receiving and measuring means corresponding to the chosen azimuthal viewing positions. Each of the means in question may consist of an individual photo-detector; alternatively, it may be an optical light-gathering system, in particular an optical fibre, whereby the light received at each particular location in turn is conveyed to a single photo-detector mounted at some convenient point remote from the actual viewing positions, or whereby the light received at each location is conveyed to a separate photodetector. The signals generated by the photodetector(s) may, as before, be amplified and passed to a suitable instrument whereby a display or record of the light intensities detected may be provided.

For the reason stated earlier, it is preferred, with any of the forms of apparatus discussed above, that the light source should be positioned so that the angle that the incident beam makes with the film normal is equal to the angle at which the reflected light is received at all azimuthal viewing positions. It is also preferred that the light source should be coupled with optical elements such that the beam of incident light is not only parallel but also gives a circular area of illumination on the film surface; for example, there may be used a light stop having a circular aperture and being suitably inclined to the direction of the beam, or alternatively a stop with an elliptical aperture placed perpendicularly to the beam.

In the case of the form of the apparatus described above in which there is a single, fixed photodetector and the reflected light is deflected by a moving mirror, the apparatus may with advantage incorporate the "double-beam" arrangement using a single photodetector which is frequently adopted in optical instruments in order to nullify the effects of fluctuation in the intensity of the light source. In this arrangement, the incident beam is from time to time diverted so as to be reflected from a surface of known reflectance characteristics (e.g. a block of pure barium sulphate) instead of from the surface of the film to be characterised.

A further possible modification of any of the forms of apparatus described above, which follows common practice in instruments of the prior art for measuring the reflectance of surface coating films, is the inclusion of a glass hemisphere to counteract the effect upon the reflectance measurements of the refractive index of the binder in the film. The hemisphere, having a refractive index similar to that of the binder, is placed with its base lying upon the film surface, with a layer of oil, also having a refractive index similar to that of the binder, in between to ensure good optical contact, in such a position that both the incident light beam and the reflected beam, when viewed from any of the various azimuthal angles, pass through it.

Figure 3:
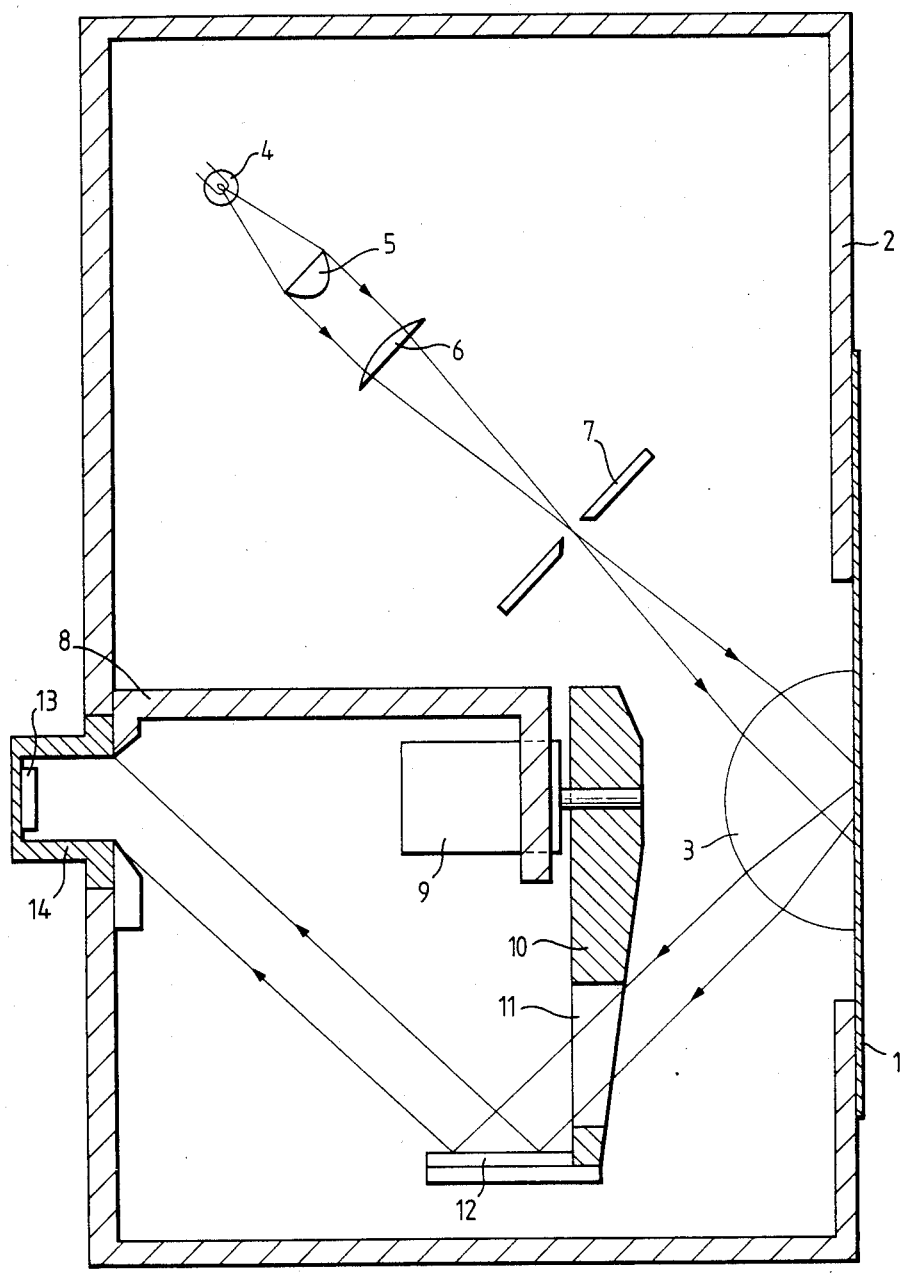
FIG. 3 shows a cross section of the apparatus.

The invention is illustrated by the following brief description of an apparatus incorporating a single, fixed photodetector and a movable viewing mirror, with reference to the accompanying FIG. 3, which is a diagrammatic cross-sectional representation of the apparatus.

A planar sample 1 (also seen in cross-section in the figure) of a coating film containing metallic flake pigment is clamped to an aperture in the side of a light-tight enclosure 2, and there is in turn clamped to the surface of the film (the clamping means are not shown) a glass hemisphere 3 of a refractive index similar to that of the binder resin in the film; the base of the hemisphere is maintained in optical contact with the film surface by means of a layer of oil (not shown) and the curved surface of the hemisphere faces into the interior of the enclosure 2. Light from a source 4 located within the enclosure passes through a condenser lens 5 and a secondary focussing lens 6 so that it is brought to a focus at an optical stop 7. The lenses are so arranged that, as the light continues and passes into the hemisphere 3, it is rendered parallel and produces an illuminated area on the surface of the film 1. A bracket 8 secured to the wall of the enclosure 2 carries a multiple stepping motor 9, upon the shaft of which is mounted an arm 10 pierced by an aperture 11 and carrying at its outer end a mirror 12. The mirror is positioned so that it always lies parallel to the axis of rotation of the arm 10 during the stepwise motion of the latter in a plane parallel to the plane of the film 1. Calibration means (not shown) are provided so that the azimuthal angle through which the arm rotates can be measured. Light reflected from the film returns through the hemisphere 3 in a variety of directions. Only that part of the light which passes through the aperture 11 is then reflected at the mirror 12 so as to strike a photodetector 13 mounted in the opposite wall of the enclosure 2. The photodetector is located at the closed end of a cylindrical member 14 the inner walls of which are painted white and the function of which is to collect all the reflected light falling upon it, irrespective of the angular position of the arm 10 and the mirror 12, and to convey a constant fraction of it to the photodetector. The relative positions of the photodetector 13, the mirror 12, the light source 4, the lenses 5 and 6 and the optical stop 7 are such that the angle at which the incident light beam falls upon the film surface is equal to the angle at which the beam reaching the photodetector via the mirror is reflected from the film surface. The photodetector 13 is connected to a suitable amplifier and recorder or meter (not shown). At each step-wise position of the arm 10, its azimuthal angular position is recorded and a reading of the intensity of the light reflected from the film sample is taken on the meter; the data thus obtained are treated in the manner described above so as to produce a graphical display of the distribution of orientation of the metallic flakes in the film sample.

TABLE

| Angle $\phi-\phi_o$ ° | Reading | Calculated Angle $\alpha$ | Calculated % Relative Reflectance |
| --- | --- | --- | --- |
| 250 | 0 | 29.8 | 0 |
| 240 | 1 | 26.5 | 3 |
| 230 | 2 | 22.9 | 6 |
| 220 | 2½ | 18.9 | 8 |
| 210 | 4½ | 14.5 | 14 |
| 205 | 8 | 12.2 | 25 |
| 200 | 11 | 9.8 | 34 |
| 195 | 15½ | 7.4 | 48 |
| 190 | 23 | 5.0 | 72 |
| 185 | 28 | 2.5 | 88 |
| 180 | 32 | 0 | 100 |
| 175 | 28 | 2.5 | 88 |
| 170 | 23 | 5.0 | 72 |
| 165 | 15½ | 7.4 | 48 |
| 160 | 11 | 9.8 | 34 |

TABLE-continued

| Angle $\phi-\phi_o$ ° | Reading | Calculated Angle $\alpha$ | Calculated % Relative Reflectance |
| --- | --- | --- | --- |
| 155 | 8 | 12.2 | 25 |
| 150 | 4½ | 14.5 | 14 |
| 140 | 2½ | 18.9 | 8 |
| 130 | 2 | 22.9 | 6 |
| 120 | 1 | 26.5 | 3 |
| 110 | 0 | 29.8 | 0 |

Angle of incident light = 45°

We claim:

1. A method for the characterisation of a surface coating film containing a metallic flake pigment, the method comprising the steps of (a) illuminating a plane specimen of the film with a parallel beam of light which is inclined at a fixed angle of incidence substantially greater than zero relative to the normal with respect to the film surface and (b) measuring the intensity of light reflected from the film at a plurality of azimuthal viewing positions at each of which there is intercepted a beam of light reflected from a point on the film surface within the illuminated area thereof, the positions being located in a circle which lies in a plane parallel to the film surface and through the centre of which the film normal at that point passes.

2. A method as claimed in claim 1, comprising the further steps of (c) expressing the intensity of light reflected at each azimuthal position as a proportion of the intensity of light reflected at some selected azimuthal position and (d) establishing the relationship between the proportional intensities so derived and the angles which the metallic flakes make with the film normal.

3. A method as claimed in claim 1, wherein the angle made with the film normal by the incident light beam is equal to the angle made with the film normal by the reflected beam intercepted at all azimuthal viewing positions.

4. A method as claimed in claim 1, wherein refraction of the incident and reflected beams at the film surface is prevented.

5. A method as claimed in claim 1 wherein the incident light beam is from time to time diverted so as to be reflected from a surface of known reflectance characteristics instead of from the surface of the film to be characterised.

6. A apparatus suitable for the characterisation of a surface coating film containing metallic flake pigment, the apparatus comprising a source for producing a parallel beam of light, a support for the film to be characterised so positioned that the beam is directed towards the film at a given angle to the normal with respect to the film surface and the film is illuminated thereby, and means for receiving the light reflected from an area of the film surface lying wholly within the illuminated area at at least four different azimuthal viewing positions located in a circle which lies in a plane parallel to the film surface and through the centre of which the normal to the film at a point within said illuminated area passes, and means for measuring the light thus received, the light source being so positioned that the angle which the incident beam makes with the film normal is equal to the angle which the reflected beam intercepted at all azimuthal viewing positions makes with the film normal.

* * * * *